(12) United States Patent  
Yamaya

(10) Patent No.: US 8,031,416 B2  
(45) Date of Patent: Oct. 4, 2011

(54) ENDOSCOPE

(75) Inventor: Koji Yamaya, Hachioji (JP)

(73) Assignee: Olympus Medical Systems Corp. (JP)

( * ) Notice: Subject to any disclaimer, the term of this patent is extended or adjusted under 35 U.S.C. 154(b) by 375 days.

(21) Appl. No.: 12/129,936

(22) Filed: May 30, 2008

(65) Prior Publication Data  
US 2009/0067067 A1 Mar. 12, 2009

(30) Foreign Application Priority Data  
Sep. 7, 2007 (JP) ................. 2007-233164

(51) Int. Cl.  
G02B 7/02 (2006.01)

(52) U.S. Cl. ..................... 359/813

(58) Field of Classification Search .......... 359/813; 600/170, 174  
See application file for complete search history.

(56) References Cited

U.S. PATENT DOCUMENTS

| 4,390,254 | A | * | 6/1983 | Yoshinaga | 359/385 |
| 6,641,530 | B2 | * | 11/2003 | Mitsumori | 600/167 |
| 2005/0259320 | A1 | * | 11/2005 | Fujimura | 359/385 |
| 2006/0250687 | A1 | * | 11/2006 | Karaki et al. | 359/368 |

FOREIGN PATENT DOCUMENTS  
JP 9-149883 6/1997  
* cited by examiner

Primary Examiner — Ricky Mack  
Assistant Examiner — Vipin Patel  
(74) Attorney, Agent, or Firm — Ostrolenk Faber LLP

(57) ABSTRACT

An optical axis restriction surface, which restricts movement of a first lens frame in an optical axis direction, and a fixing slit, which is located in rear of the optical axis restriction surface, are formed on an end portion of a second lens frame. Lens frame hold portions, which restrict rotation of the first lens frame about an optical axis and movement of the first lens frame in a right-and-left direction, are formed on both sides of the fixing slit. The lens frame hold portions are provided with assembly reference surfaces which restrict movement of the first lens frame in an up-and-down direction. An engaging portion, which is engaged with the fixing slit, and two projection portions, which come in contact with the assembly reference surfaces, are formed on the first lens frame.

10 Claims, 10 Drawing Sheets

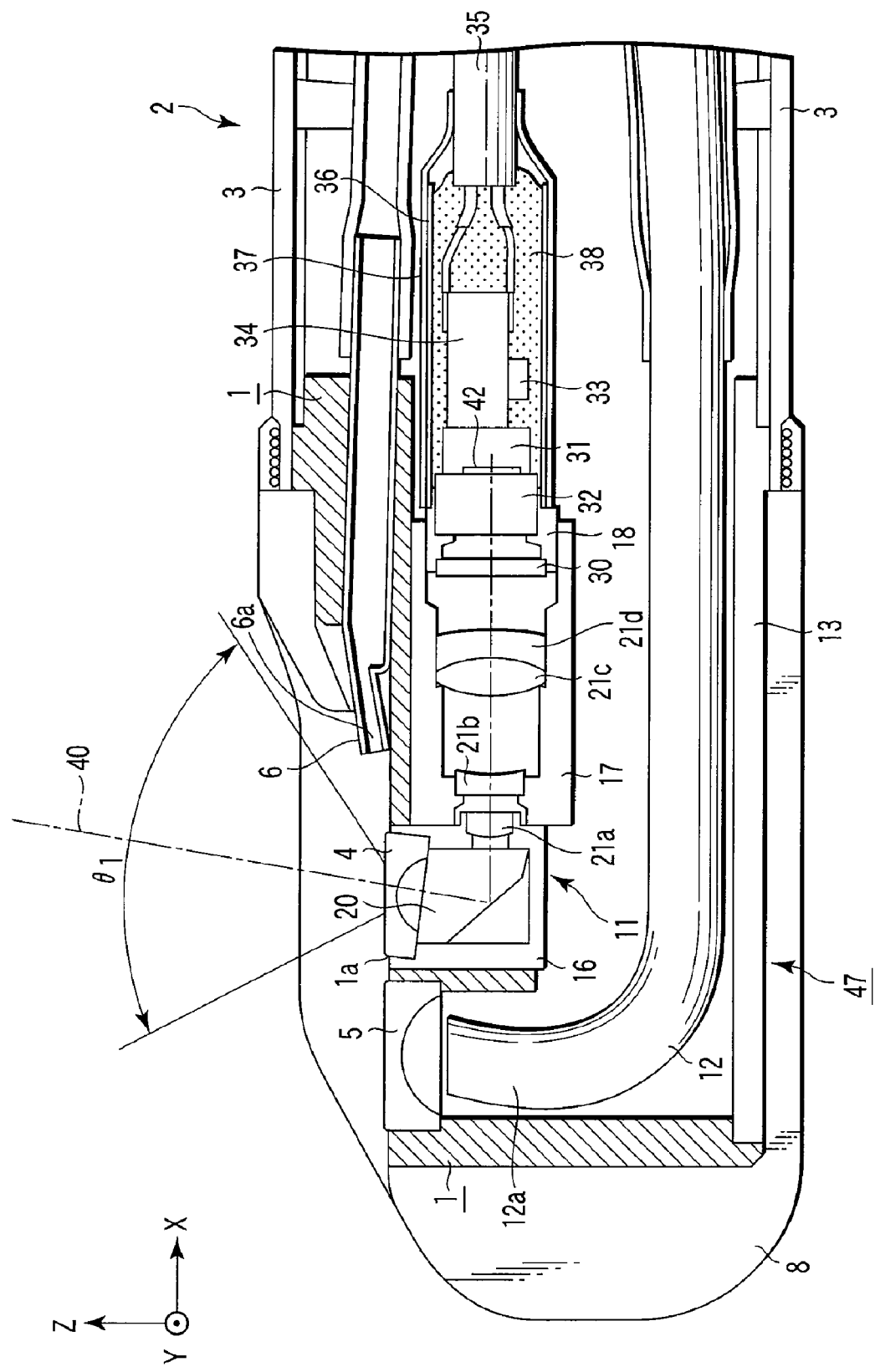
F I G. 1

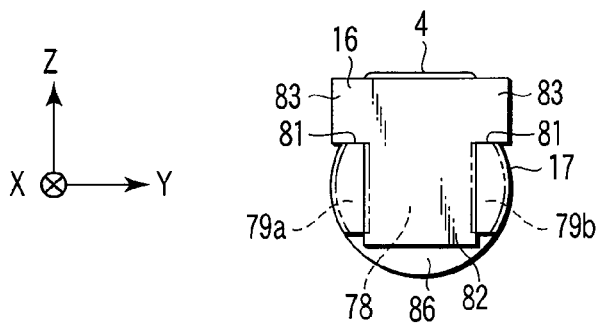
F I G. 6A
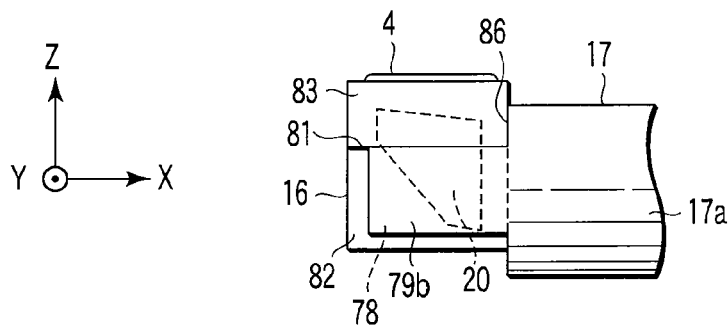
F I G. 6B
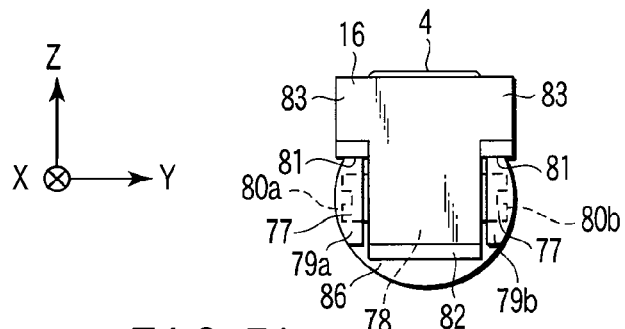
F I G. 7A
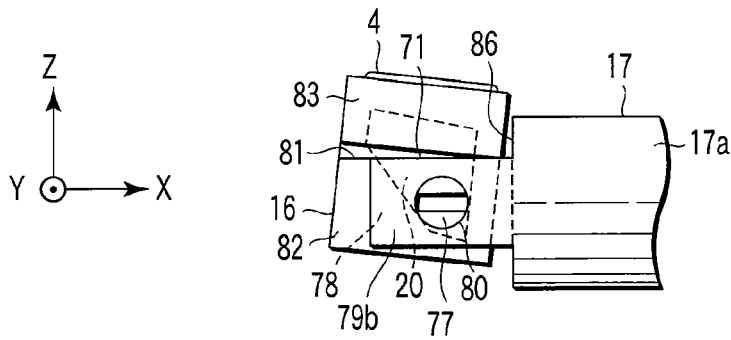
F I G. 7B

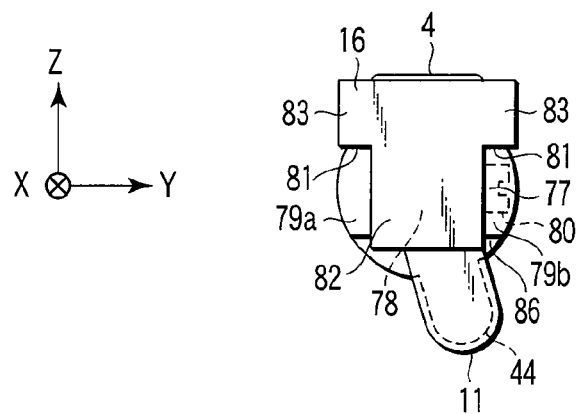
F I G. 12A
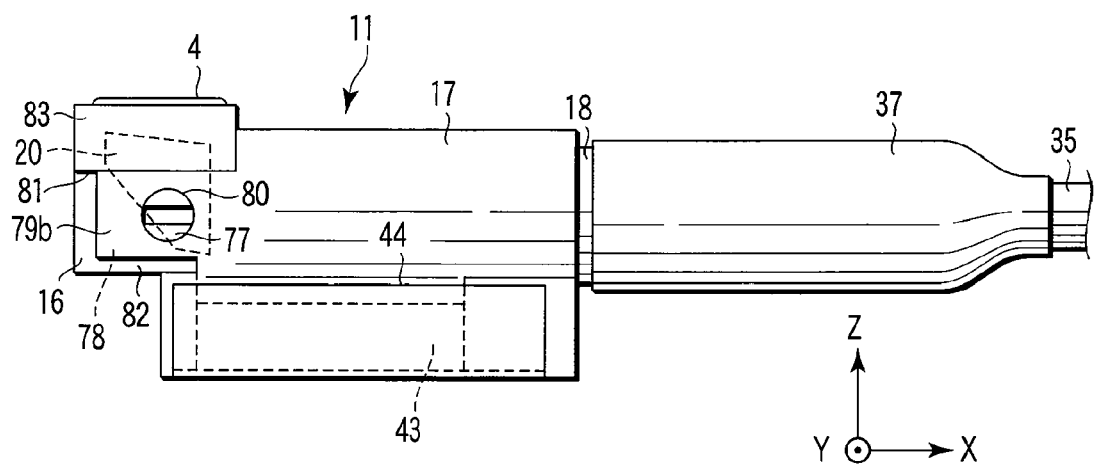
F I G. 12B
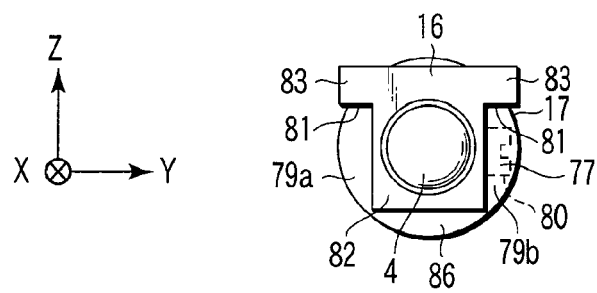
F I G. 13A

ENDOSCOPE

CROSS-REFERENCE TO RELATED APPLICATIONS

This application is based upon and claims the benefit of priority from prior Japanese Patent Application No. 2007-233164, filed Sep. 7, 2007, the entire contents of which are incorporated herein by reference.

BACKGROUND OF THE INVENTION

1. Field of the Invention

The present invention relates to an endoscope including an objective optical system which guides an observation image to an image pickup element while varying a direction of guide by a prism.

2. Description of the Related Art

Jpn. Pat. Appln. KOKAI Publication No. H09-149883, for instance, discloses a side-viewing electronic endoscope which can exactly and easily dispose an optical axis of an objective optical system. In this side-viewing electronic endoscope, the objective optical system including a prism is precisely composed of two units by two frame members. Further, the two units are assembled by using position restriction means which comprises an engaging groove and a projection portion, whereby rotation about the axis is restricted (corresponding restriction in an up-and-down direction and restriction in a right-and-left direction) and back-and-forth movement in the axial direction is restricted (focus position adjustment). Thereby, in the side-viewing electronic endoscope, the optical axis is exactly and easily disposed in the normal position, and the optical performance is ensured.

BRIEF SUMMARY OF THE INVENTION

In consideration of the above, in order to obtain a good observation image, the present invention provides an endoscope which can perform optical axis adjustment between two units in multiple directions with a simple structure, without occupying a space.

According to the present invention, there is provided an endoscope comprising: a front group optical frame which holds a first objective optical system; a rear group optical frame which holds a second objective optical system; an objective optical system which is composed of at least two optical frames which are the front group optical frame and the rear group optical frame; a front group engaging section which is formed on the front group optical frame; a rear group engaging section which is formed on the rear group optical frame and is to be engaged with the front group engaging section; coupling support means for engaging the front group engaging section and the rear group engaging section, thereby coupling and supporting the front group optical frame relative to the rear group optical frame such that rotation of the front group optical frame about an optical axis, relative to the rear group optical frame, is restricted, the front group optical frame is adjustably movable along an optical axis direction relative to the rear group optical frame, and the front group optical frame is adjustably movable rotationally about an axis perpendicular to the optical axis, relative to the rear group optical frame; and a fixing section which integrally fixes the front group optical frame, a position of disposition of which is adjusted by the coupling support means, and the rear group optical frame.

According to the present invention, there is provided an endoscope comprising: a front group optical frame which holds a first objective optical system; a rear group optical frame which holds a second objective optical system and is disposed in front of the front group optical frame in a direction of travel of light; an objective optical system which is composed of at least two optical frames which are the front group optical frame and the rear group optical frame; an optical axis in the second objective optical system; a Y axis which is perpendicular to an axial direction of the optical axis; a Z axis which is perpendicular to the axial direction of the optical axis and an axial direction of the Y axis; a front group engaging section which is formed on the front group optical frame; a rear group engaging section which is formed on the rear group optical frame and is engaged with the front group engaging section, thereby to couple the front group optical frame and the rear group engaging section; adjusting means for restricting, when the front group engaging section and the rear group engaging section are engaged and the front group optical frame and the rear group engaging section are coupled, rotation of the front group optical frame in a circumferential direction about the axial direction of the optical axis, relative to the rear group optical frame, moving the front group optical frame in the axial direction of the optical axis, relative to the rear group optical frame, and moving rotationally the front group optical frame in a circumferential direction about the axial direction of the Y axis, relative to the rear group optical frame, thereby adjusting a position of disposition of the front group optical frame relative to the rear group optical frame; and a fixing section which integrally fixes the front group optical frame, the position of disposition of which is adjusted by the adjusting means, to the rear group optical frame.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a cross-sectional view of a distal end section of a side-viewing electronic endoscope according to a first embodiment of the present invention;

FIG. 6A is a front view showing a first modification of the connection structure of a first lens frame and a second lens frame in the first embodiment;

FIG. 6B is a side view showing the first modification of the connection structure of the first lens frame and the second lens frame in the first embodiment;

FIG. 7A is a front view showing a second modification of the connection structure of the first lens frame and the second lens frame in the first embodiment;

FIG. 7B is a side view showing the second modification of the connection structure of the first lens frame and the second lens frame in the first embodiment;

FIG. 12A is a front view of an objective optical system unit;

FIG. 12B is a side view of the objective optical system unit;

FIG. 13A is a front view of an objective optical system unit in a forward-viewing electronic endoscope according to a third embodiment of the invention;

DETAILED DESCRIPTION OF THE INVENTION

Embodiments of the present invention will now be described with reference to the accompanying drawings.

A first embodiment is described with reference to FIG. 1 to FIG. 5.

In the description below, an X axis direction (e.g. a right-and-left direction in FIG. 1) refers to a longitudinal axis direction of an objective optical system unit, and is an axial direction of an optical axis 40 (optical axis direction) in a second lens frame 17. A direction perpendicular to the X axis direction is defined as a Y axis direction, which is a width direction of the objective optical system unit. A direction perpendicular to the X axis direction and Y axis direction is defined as a Z axis direction (e.g. an up-and-down direction in FIG. 1). Thus, the Y axis direction and the Z axis direction are perpendicular to the optical axis direction.

Figure 5:
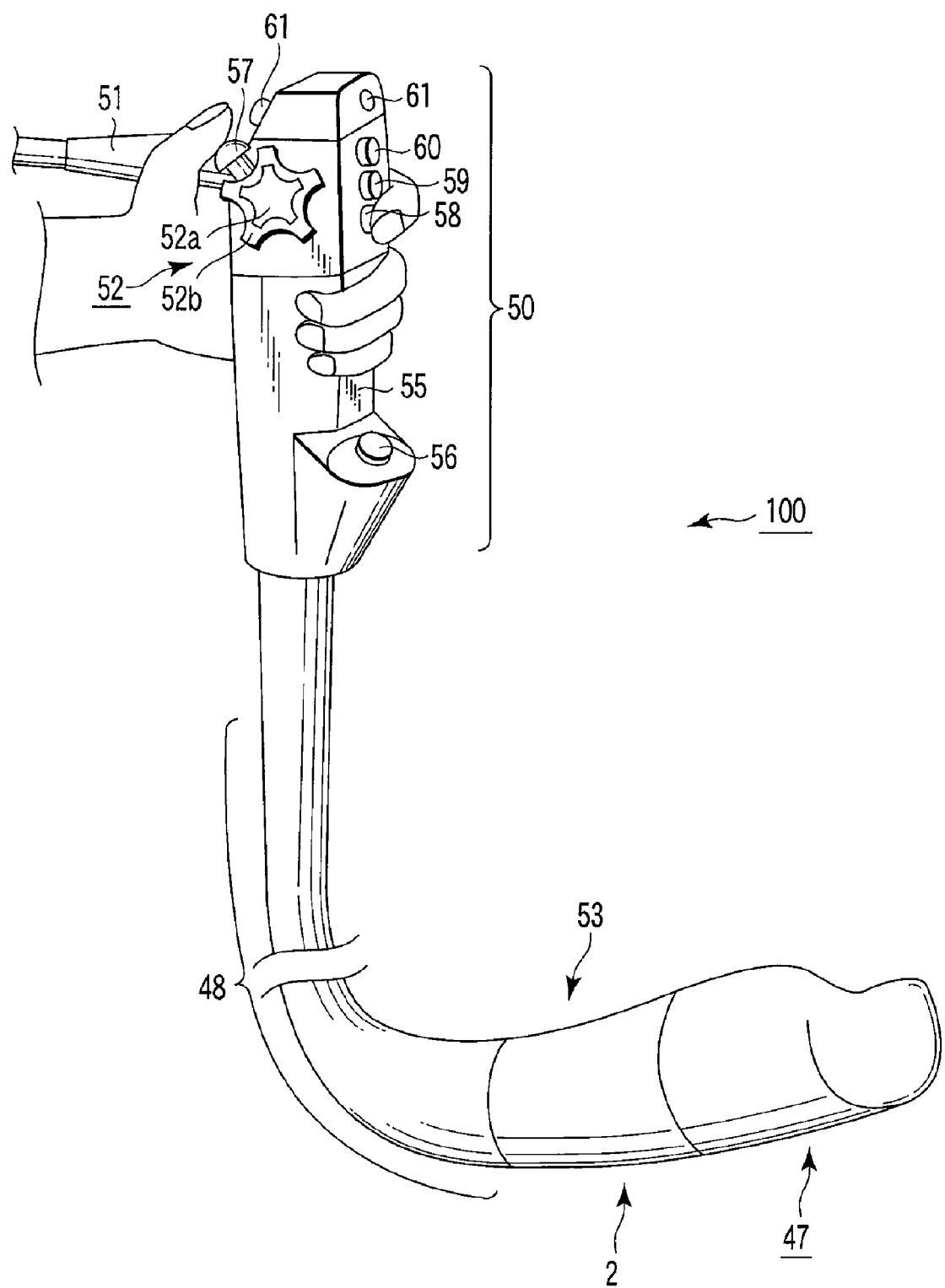
FIG. 5 is a schematic perspective view of the endoscope according to the first embodiment.

An endoscope 100 in the present embodiment shown in FIG. 1 and FIG. 5 is a side-viewing electronic endoscope having a view field, for example, in a direction (Z axis direction) perpendicular to the direction of insertion of an insertion section 53. As shown in FIG. 5, a distal end section 47, which is disposed at a foremost end of the insertion section 53 of the endoscope 100, includes a distal end section body 1 shown in FIG. 1. The distal end section body 1 is formed of a metal such as stainless steel. A proximal end of the distal end section body 1 is coupled to a distal end of a bending section 2, as shown in FIG. 1. The bending section 2 is disposed at an intermediate part of the insertion section 53 having flexibility. An outer surface of the bending section 2 is formed of, e.g. coating rubber 3, which is a soft, elastic member.

A flat surface portion 1a is formed on a side surface of the distal end section body 1. In the flat surface portion 1a, there are disposed an illumination window 5 which transmits through light for illuminating, for example, a mucous membrane, which is a part to be observed, for example, in a body cavity; an observation window 4 which neighbors the illumination window 5 and on which reflective light of the light that has been transmitted from the illumination window 5 and reflected by the mucous membrane is made incident in order to observe the mucous membrane; an air-supply/water-supply nozzle 6 which is fixed to the distal end section body 1 in order to supply air or water to the mucous membrane; and an endo-therapy product projection port (not shown) from which an endo-therapy product (not shown) projects.

The observation window 4, illumination window 5 and air-supply/water-supply nozzle 6 are arranged in the longitudinal direction of the distal end section body 1. The observation window 4 is disposed more on the proximal end side of the distal end section body 1 than the illumination window 5. The air-supply/water-supply nozzle 6 is disposed more on the proximal end side of the distal end section body 1 than the observation window 4. In addition, as shown in FIG. 1, a nozzle face 6a of the air-supply/water-supply nozzle 6 is directed to the observation window 4 and illumination window 5.

An electrically insulative distal end cap 8 is coated and fixed on the outer peripheral surface of the distal end section body 1, except the flat surface portion 1a where the observation window 4 and illumination window 5 are disposed, and an opening portion of the endo-therapy product projection port. At the rear end of the distal end cap 8, the coating rubber 3 is watertightly attached to the distal end section body 1. In FIG. 1, the distal end cap 8 is configured to be fixed to the distal end section body 1. However, the structure of the distal end cap 8 is not limited to this, and the distal end cap 8 may be configured to be detachably attached to the distal end section body 1.

In the distal end section body 1, an objective optical system unit 11 including the observation window 4 is disposed as a single unit. The objective optical system unit 11 is disposed under the flat surface portion 1a.

A light guide fiber 12 is disposed under the objective optical system unit 11 in the same direction as the objective optical system unit 11. The light guide fiber 12 transmits (guides) light, which is emitted from a light source device (not shown), to the illumination window 5. A distal end portion 12a of the light guide fiber 12 is bent so as to be connected to the illumination window 5 from under the objective optical system unit 11. A cover member 13, which covers the light guide fiber 12 at the distal end section body 1, is disposed on the outside of the light guide fiber 12. The cover member 13 is bonded to the distal end section body 1. At the rear end of the distal end cap 8, the coating rubber 3 is watertightly attached to the cover member 13.

Next, referring to FIG. 1, the objective optical system unit 11 is described in brief.

The objective optical system unit 11, which is a single unit, is composed of three small units, namely, a first lens frame 16 that is a front group optical frame, a second lens frame 17 that is a rear group optical frame, and a third lens frame 18. The first lens frame 16, second lens frame 17 and third lens frame 18 are arranged from the distal end side of the objective optical system unit 11 in the X axis direction. The second lens frame 17 is disposed in front of the first lens frame 16 in the direction of travel of light.

In the first lens frame 16, there are fixed and disposed the observation window 4; a prism 20 which reflects the reflective light transmitting through the observation window 4 and varies the progress of the light (i.e. deflects the optical axis 40); and a convex lens that is a first lens 21a which passes the reflective light that is reflected by the prism 20. The observation window 4, prism 20 and first lens 21a are successively arranged from the distal end side of the objective optical system unit 11 in the direction of travel of the reflective light. The observation window 4, prism 20 and first lens 21a constitute a first objective optical system.

In the second lens frame 17, there are fixed and disposed a concave lens which is a second lens 21b which transmits through the reflective light that has transmitted through the first lens 21a; a convex lens which is a third lens 21c for transmitting through the reflective light transmitting through the second lens 21b; and a concave lens which is a fourth lens 21d which transmits through the reflective light transmitting through the third lens 21c. The second lens 21b, third lens 21c and fourth lens 21d constitute a second objective optical system. The prism 20 is not included in the second objective optical system.

In the third lens frame 18, an optical filter 30 which shades, e.g. infrared light, and transmits through visible light, and a cover glass 32 which is formed integral with an image pickup element 31, such as a CCD, are disposed along the X axis direction. The image pickup element 31 receives the reflective light, which is transmitted through the optical filter 30, on its light-receiving surface (photodetector?) 42, and converts the reflective light to an electric signal that is a video signal.

The above-described image pickup element 31, an electric board 34 which is connected to the image pickup element 31, and a signal cable 35 which is connected to the electric board 34 are successively disposed from the distal end side in the X axis direction.

An electric component 33 is mounted on the electric board 34, and the electric board 34 amplifies the electric signal. The signal cable 35 transmits the electric signal to a video processor (not shown).

The outside (outer periphery) of the image pickup element 31 and electric board 34 is protected by a thin metal plate 36 having a complete circumferential shape. The outside of the metal plate 36 is coated with an electrically insulative tube 37. An adhesive 38 is filled between the electric board 34, signal cable 35 and metal plate 36. Thereby, the third lens frame 18, image pickup element 31, electric board 34, signal cable 35 and metal plate 36 are constituted as one unit.

As described above, the first lens frame 16, second lens frame 17 and third lens frame 18 include lenses, respectively.

The first lens frame 16 is optically aligned with, and bonded and fixed to, the second lens frame 17.

The third lens frame 18 is optically aligned with, and bonded and fixed to, the second lens frame 17.

A dot-and-dash line in FIG. 1 indicates an optical axis 40. The optical axis 40 is reflected by the prism 20 and made substantially parallel with the X axis direction within the objective optical system unit 11, and is focused on the light-receiving surface 42. The optical axis 40 is the optical axis in the first objective optical system and the second objective optical system.

A subject image focused on the light-receiving surface 42 is converted to an electric signal by the image pickup element 31, and then amplified and transmitted to the video processor (not shown) via the signal cable 35. Further, the subject image is subjected to signal processing in the video processor and is displayed as an observation image on a monitor (not shown).

In the objective optical system unit 11, an adhesive (not shown) is coated on coupling parts between the first lens frame 16, second lens frame 17 and third lens frame 18 over the entire region. Thereby, foreign matter (i.e. moisture, water drops, dust) is prevented from entering the objective optical system unit 11 including these coupling parts from the outside of the objective optical system unit 11.

The angle (angle of view field) θ1 in FIG. 1 indicates the angle of view field. The whole lens structure is not limited to that shown in FIG. 1.

In general, in the case of the side-viewing electronic endoscope, the distal end section body 1 is provided with the above-described endo-therapy product projection port (not shown). An endo-therapy product raising base (not shown), which can be remotely operated to make oscillating movement in accordance with a raising operation on the proximal side of an operation section 50 (to be described later), is stored in the endo-therapy product projection port. Specifically, the endo-therapy product raising base makes oscillating movement between a stored position where the endo-therapy product raising base is stored in the distal end section body 1 (the endo-therapy product projection port), and a raised position where the endo-therapy product raising base is projected (raised) from the flat surface portion 1a of the distal end section body 1, that is, from the endo-therapy product projection port. To be more specific, a raising operation wire (not shown), for instance, is pushed and pulled in accordance with the raising operation on the proximal side of the operation section (to be described later), and thereby the endo-therapy product raising base is freely moved rotationally relative to the distal end section body 1 about a support shaft (not shown) and makes oscillating movement between the stored position and the raised position.

The endo-therapy product raising base is moved rotationally (oscillated) in accordance with the raising operation, guides the endo-therapy product, and projects the endo-therapy product from the endo-therapy product projection port.

Figure 2:
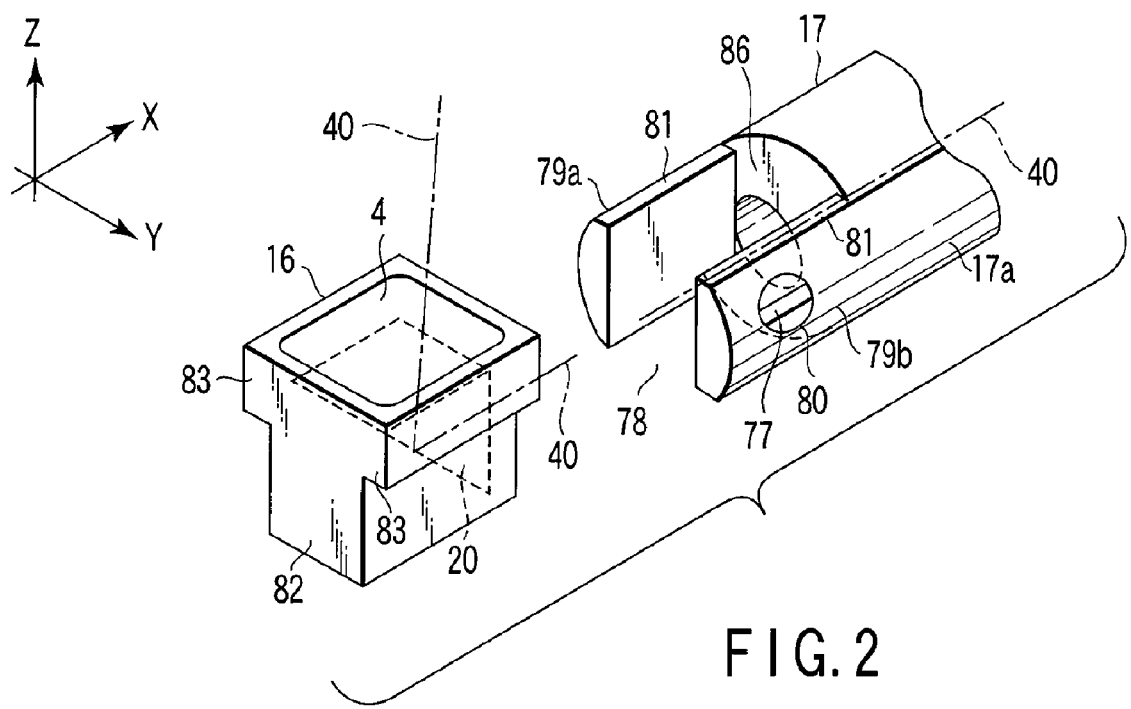
FIG. 2 is an exploded perspective view showing a connection part between a front group optical frame and a rear group optical frame shown in FIG. 1.

Next, referring to FIG. 2 to FIG. 4, the objective optical system unit 11 is described in detail.

As shown in FIG. 2, an end portion 17a of the second lens frame 17, which is the rear group optical frame, is provided with an optical axis restriction surface 86; a fixing slit 78 which is disposed in front of the optical axis restriction surface 86 in the direction of travel of reflective light, and substantially in parallel to the optical axis 40; and a pair of lens frame hold portions 79a and 79b which are in contact with the optical axis restriction surface 86 and extend in the optical axis direction on both sides of the fixing slit 78.

Figure 3A:
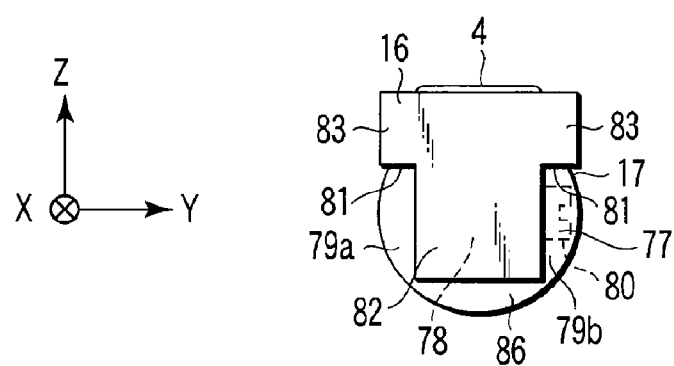
FIG. 3A is a front view of an objective optical system unit.
Figure 3B:
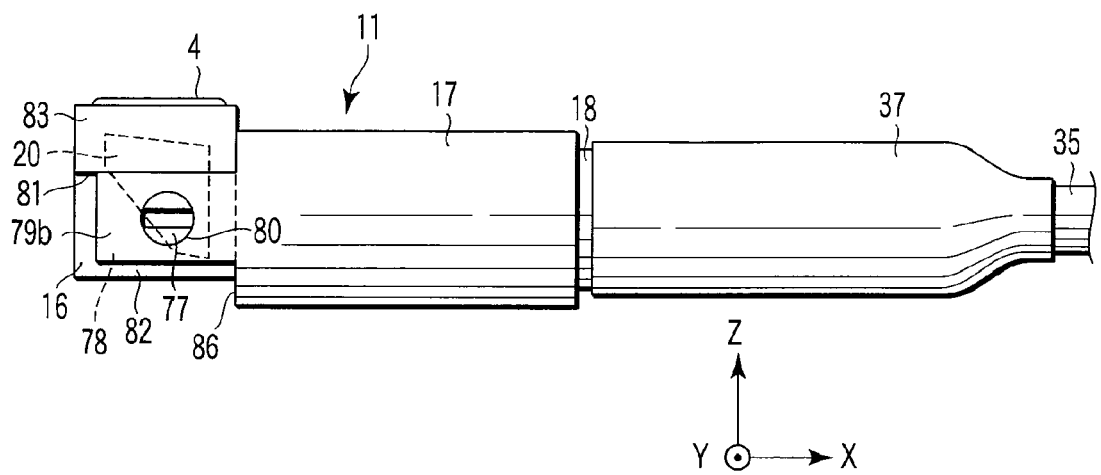
FIG. 3B is a side view of the objective optical system unit.

As shown in FIG. 3B, the first lens frame 16 is put in contact with the optical axis restriction surface 86. At this time, the optical axis restriction surface 86 restricts movement of the first lens frame 16 in the optical axis direction. Thus, the optical axis restriction surface 86 is an optical axis direction restriction section which restricts the position of the first lens frame 16 in the optical axis direction to a predetermined position, and is a first restriction section which restricts the position of disposition of the first lens frame 16 in the optical axis direction.

The fixing slit 78 is a gap portion which is interposed between the lens frame hold portions 79a and 79b in the Y axis direction. The fixing slit 78 is formed along the optical axis direction.

The lens frame hold portions 79a and 79b are hold portions which hold projection portions 83 (to be described later). The lens frame hold portions 79a and 79b are opposed to each other in the Y axis direction, and restrict rotation of the first lens frame 16 about the optical axis 40 and movement of the first lens frame 16 in the Y axis direction. Thus, the lens frame hold portions 79a and 79b are a perpendicular direction restriction section which restricts the position of the first lens frame 16 in a direction (e.g. Y axis direction) perpendicular to the optical axis 40 to a predetermined position, and are a second restriction section which restricts the position of disposition of the first lens frame 16 in the Y axis direction.

A screw hole 80 which communicates with the fixing slit 78 is formed in, and penetrates, the lens frame hold portion 79b. A screw 77, which is a fixing section, is engaged in the screw hole 80. The screw 77 integrally fixes the first lens frame 16, the position of disposition of which is adjusted by coupling support means (adjusting means) (to be described later), and the second lens frame 17. Thereby, the first lens frame 16 is aligned with, and fixed to, the second lens frame 17.

Assembly reference surfaces 81, which restrict movement of the first lens frame 16 in the Z axis direction, to be more specific, in a minus-side direction of the Z axis, are formed on the lens frame hold portions 79a and 79b. The assembly reference surfaces 81 are not restrictively used, and may be replaced with edge lines. Thus, the assembly reference surfaces 81 are a perpendicular direction restriction section which restricts the position of the first lens frame 16 in a direction (e.g. Z axis direction) perpendicular to the optical axis 40 to a predetermined position, and are a third restriction section which restricts the position of disposition of the first lens frame 16 in the Z axis direction.

As shown in FIG. 2, the first lens frame 16 has, for example, a substantially T-shaped form. The first lens frame 16 is provided with an engaging portion 82 which is engaged with the fixing slit 78, and two projection portions 83 which come in contact with the assembly reference surfaces 81 and are held by the lens frame hold portions 79a and 79b when the engaging portion 82 is engaged with the fixing slit 78. The prism 20 is disposed in the engaging portion 82, as indicated by a broken line.

In the present embodiment, as shown in FIG. 3A, the length of the engaging portion 82 (the width of the engaging portion 82) in the Y axis direction is substantially equal to the length of the fixing slit 78 (the width of the fixing slit 78) which is the length between the lens frame hold portions 79a and 79b.

In this manner, the engaging portion 82 and the projection portions 83 constitute a front group engaging section which is formed on the first lens frame 16. The fixing slit 78, the lens frame hold portions 79a and 79b and the assembly reference surfaces 81 constitute a rear group engaging section which is formed on the second lens frame 17 and is to be engaged with the front group engaging section in order to connect (couple) the first lens frame 16 and the second lens frame 17.

When the first lens frame 16 and the second lens frame 17 are connected, the first lens frame 16 moves toward the second lens frame 17 in the optical axis direction and comes in contact with the optical axis restriction surface 86. Thereby, the movement of the first lens frame 16 in the optical axis direction is restricted by the optical axis restriction surface 86.

As regards the first lens frame 16, the engaging portion 82 is engaged with the fixing slit 78, and thus the projection portions 83 are held by the lens frame hold portions 79a and 79b. Thereby, the rotation of the first lens frame 16 in a circumferential direction about the optical axis and the movement thereof in the Y axis direction are restricted. In addition, the movement of the first lens frame 16 in the Z axis direction and the rotation thereof about the Z axis are restricted.

In this manner, the position of disposition of the first lens frame 16, relative to the second lens frame 17, is adjusted. After the adjustment, as shown in FIG. 3A and FIG. 3B, the first lens frame 16 is aligned with, and fixed to, the second lens frame 17 by the screw 77, and the first lens frame 16 is integrally coupled to the second lens frame 17. Thereafter, the first lens frame 16 and the second lens frame 17 are watertightly bonded at the boundary part over the entire circumference.

Figure 4A:
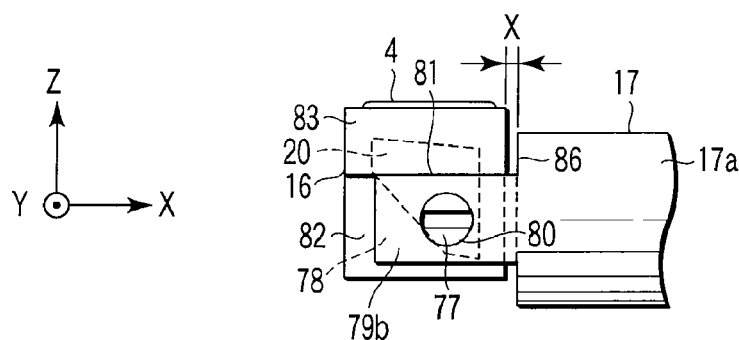
FIG. 4A is a side view showing that the front group optical frame is adjustable relative to the rear group optical frame in multiple directions by the connection structure shown in FIG. 2.

In addition to the above, the position of disposition of the first lens frame 16 is adjustable in multiple directions, relative to the second lens frame 17. For example, as shown in FIG. 4A, the first lens frame 16 may be disposed apart from the second lens frame 17 by a desired slight length X in the optical axis direction. This length X is a length from the optical axis restriction surface 86 to the first lens frame 16.

For example, the position of disposition of the first lens frame 16 is moved and adjusted from the state shown in FIG. 3B to the state shown in FIG. 4A, and thereby the optical path length can be increased by the desired length X. After the adjustment, the screw 77 is engaged in the screw hole 80, as described above, and touches on the first lens frame 16. Thus, the first lens frame 16 is aligned with, and fixed to, the second lens frame 17.

In general, the objective optical system unit 11 including, for instance, the first lens frame 16 and second lens frame 17, is fabricated by mechanical machining. Consequently, even if the respective structural parts are the same components, the dimensions of finished parts vary slightly. This being the case, when the structural parts are coupled, optical alignment and adjustment are required. By the optical adjustment, the optical performance of the whole objective optical system unit 11 is ensured.

Figure 4B:
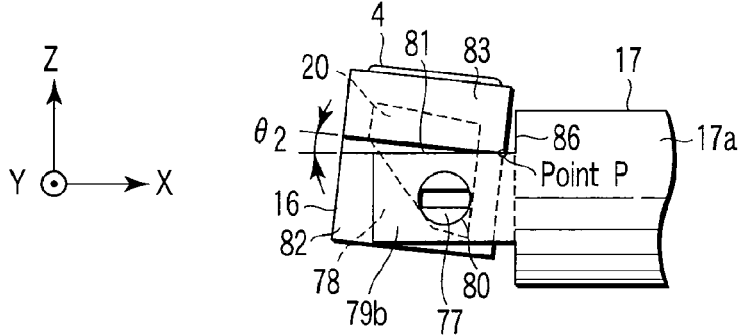
FIG. 4B is a side view showing that the front group optical frame is adjustable relative to the rear group optical frame in multiple directions by the connection structure shown in FIG. 2.

The adjustment is not limited to the increase of the optical path length, as described above. For example, from the state shown in FIG. 4A in which the optical path length is increased, the first lens frame 16 may be moved rotationally on a point P in a circumferential direction about the Y axis, as shown in FIG. 4B, in the state in which the movement of the first lens frame 16 in the Y axis direction is restricted (fixed) by the lens frame hold portions 79. In FIG. 4B, the position of disposition of the first lens frame 16 is adjusted, from the state shown in FIG. 4A, such that the first lens frame 16 is inclined by a desired small angle $\theta 2$ to the optical axis 40 in the second lens frame 17, with the point P being the vertex of the angle.

FIG. 4B shows the state in which the optical axis 40 on the front side of the prim 20 in the first lens frame 16 is aligned and adjusted relative to the optical axis 40 in the second lens frame 17. After the adjustment, the screw 77 is engaged in the screw hole 80, as described above, and touches on the first lens frame 16. Thereby, the first lens frame 16 is aligned and fixed to the second lens frame 17.

The projection portions 83 in FIG. 4B are put in point-contact with the assembly reference surfaces 81 at only the point 2, unlike the surface-contact as shown in FIG. 3B or FIG. 4A. In this case, the assembly reference surfaces 81 restrict the movement of the first lens frame 16 in a circumferential direction about the Z axis, and the movement of the first lens frame 16 in a circumferential direction about the Y axis.

In this manner, when the first lens frame 16 and the second lens frame 17 are connected, the engaging portion 82, the projection portions 83, the lens frame hold portions 79a and 79b, the assembly reference surfaces 81 and the optical axis restriction surface 86 function as coupling support means for coupling and supporting the first lens frame 16 relative to the second lens frame 17 in such a manner that the rotation of the first lens frame 16 about the optical axis (X axis) relative to the second lens frame 17 is restricted, the first lens frame 16 is adjustably movable relative to the second lens frame 17 in the optical axis direction, and the first lens frame 16 is adjustably movable rotationally relative to the second lens frame 17 in a circumferential direction about the Y axis, which is a circumferential direction about an axis perpendicular to the optical axis 40.

In other words, the coupling support means restricts the rotation of the first lens frame 16 about the optical axis (X axis) relative to the second lens frame 17. This optical axis is the above-described optical axis 40. In addition, the coupling support means couples and supports the first lens frame 16 and second lens frame 17 such that the first lens frame 16 is adjustably movable along the optical axis direction (X axis direction) relative to the second lens frame 17. Further, the coupling support means couples and supports the first lens frame 16 and second lens frame 17 such that the first lens frame 16 is adjustably movable rotationally about the Y axis relative to the second lens frame 17.

To be more specific, when the first lens frame 16 and second lens frame 17 are coupled, the engaging portion 82, the projection portions 83, the lens frame hold portions 79a and 79b, the assembly reference surfaces 81 and the optical axis restriction surface 86 function as adjusting means for restricting the rotation of the first lens frame 16 in a circumferential direction about the optical axis, relative to the second lens frame 17; restricting the movement of the first lens frame 16 in the Y axis direction relative to the second lens frame 17; restricting the rotation of the first lens frame 16 in a circumferential direction about the Z axis, relative to the second lens frame 17; moving the first lens frame 16 in the optical axis direction, relative to the second lens frame 17; rotating the first lens frame 16 about the Y axis, relative to the second lens frame 17, thereby adjusting the position of disposition of the first lens frame 16 relative to the second lens frame 17.

Although not shown, if the first lens frame 16 is not moved rotationally as shown in FIG. 4B, the position of disposition of the first lens frame 16 may be adjusted from the state shown in FIG. 4A such that the projection portions 83 are disposed upward away from the assembly reference surfaces 81 by a desired small length Z. In this manner, the position of disposition of the first lens frame 16 may be moved along the Z axis from the state shown in FIG. 4A.

Thus, the above-described coupling support means may couple and support the first lens frame 16 and second lens frame 17 so that the first lens frame 16 is adjustably movable in the Z axis direction, which is perpendicular to the optical axis 40, relative to the second lens frame 17. In other words, the adjusting means may adjust the position of disposition of the first lens frame 16 relative to the second lens frame 17 by moving the first lens frame 16 relative to the second lens frame 17 in the Z axis direction.

In FIG. 4A and FIG. 4B, since the length X and angle θ2 are very small, when the cover member is watertightly attached to the objective optical system unit 11 by the adhesive, as described above, the cover member can prevent foreign matter (i.e. moisture, water drops, dust) from entering the objective optical system unit 11.

Next, referring to FIG. 5, the endoscope 100 is described in brief.

The endoscope 100 includes an elongated insertion section 53 which is inserted, for example, in a body cavity of a patient; and an operation section 50 which is coupled to a proximal-side end portion of the insertion section 53 and operates the insertion section 53.

The insertion section 53 includes a flexible tube portion (flexible insertion tube portion) 48, a bending section 2 and the distal end section 47, in the named order from the operation section 50 side. Specifically, the operation section 50 is coupled to a proximal end of the elongated flexible tube portion (flexible insertion tube portion) 48. A distal end of the flexible tube portion 48 is coupled to a proximal end of the bending section 2. A distal end of the bending section 2 is coupled to a proximal end of the distal end section 47.

The bending section 2 is bent in four directions, namely, upward, downward, leftward and rightward directions, by the operation of a bending operation knob 52 (to be described later). Thereby, the distal end section 47, which is coupled to the bending section 2, bends in the same direction as the bending section 2.

The operation section 50 is provided with a hold portion 55 which is grasped by a surgeon, and a bending operation knob 52 which bends the bending section 2.

A proximal end portion of a universal cord 51 is coupled to the hold portion 55. A distal end portion of the universal cord 51 is connected to a light source device (not shown) which emits light, and to a connector section (not shown) for connection to a video processor.

The light guide fiber 12, for instance, is passed through the universal cord 51, flexible tube portion 48 and bending section 2. Light that is emitted from the light source device is guided via the light guide fiber 12 and is radiated from the illumination window 5 onto a part to be observed. The signal cable 35, for instance, is passed through the flexible tube portion 48 and bending section 2.

The bending operation knob 52 is provided with a right-and-left bending operation knob 52a for bending the bending section 2 in a right-and-left direction, and an up-and-down bending operation knob 52b for bending the bending section 2 in an up-and-down direction. A right-and-left bending operation mechanism (not shown), which is driven by the right-and-left bending operation knob 52a, is connected to the right-and-left bending operation knob 52a. An up-and-down bending operation mechanism (not shown), which is driven by the up-and-down bending operation knob 52b, is connected to the up-and-down bending operation knob 52b. The right-and-left bending operation mechanism and the up-and-down bending operation mechanism are disposed in the operation section 50, and are connected to proximal end portions of operation wires (not shown) for bending the bending section 2 in the upward, downward, leftward and rightward directions.

The operation section 50 is provided with a endo-therapy product insertion portion 56 which is a proximal-side opening portion of an endo-therapy product insertion channel (not shown) communicating with the endo-therapy product projection port of the distal end section 47; an endo-therapy product raising base operation lever 57 for raising the endo-therapy product raising base by a remote operation using, e.g. a raising operation wire; an air-supply/water-supply button 58 for supplying air or water from the air-supply/water-supply nozzle 6 toward the observation window 4, etc.; a suction button 59 for a suction operation for suction from the distal end section 47 via a suction channel (not shown) which is branched from the endo-therapy product insertion channel (not shown) in the operation section 50; a release switch 60 which stores an observation image in a memory section (not shown); and an image process switch 61 for an image process of the observation image.

Next, a description is given of a method of aligning the position of disposition of the first lens frame 16 relative to the second lens frame 17, and adjusting the optical axis.

The engaging portion 82 is engaged with the fixing slit 78, and the first lens frame 16 is engaged with the second lens frame 17. At this time, as shown in FIG. 3B and FIG. 4A, if the projection portions 83 come in surface-contact with the assembly reference surfaces 81, the movement of the first lens frame 16 in the Z axis direction is restricted by the assembly reference surfaces 81. In addition, when the engaging portion 82 is held by the lens frame hold portions 79a and 79b, the rotation of the first lens frame 16 about the X axis and the movement thereof in the Y axis direction are restricted.

For example, as shown in FIG. 3B, if the first lens frame 16 comes in contact with the optical axis restriction surface 86, the movement of the first lens frame 16 in the optical axis direction is restricted. Thereby, the position of disposition of the first lens frame 16 in the optical axis direction is adjusted.

For example, as shown in FIG. 4A, the movement of the first lens frame 16 in the optical axis direction may be restricted such that the first lens frame 16 is spaced apart from the optical axis restriction surface 86 by a desired small length X. Thereby, the position of disposition of the first lens frame 16 in the optical axis direction is adjusted.

As shown in FIG. 4B, the of the first lens frame 16 in the circumferential direction about the Y axis may be restricted such that the first lens frame 16 is inclined by a desired small angle θ2 to the optical axis 40, with the point P being the vertex of the angle. Thereby, the position of disposition of the first lens frame 16 in the circumferential direction about the Y axis is adjusted. At this time, the of the first lens frame 16 in the circumferential direction about the Z axis is restricted by the assembly reference surfaces 81.

In addition, if the first lens frame 16 is not moved rotationally as shown in FIG. 4B, the movement of the first lens frame 16 in the Z axis direction may be restricted such that the projection portions 83 are disposed upward away from the assembly reference surfaces 81 by a desired small length Z.

If the position of disposition of the first lens frame 16 relative to the second lens frame 17 is adjusted in this manner, the screw 77 is engaged in the screw hole 80 and touches on the first lens frame 16. Thus, the first lens frame 16 is aligned with and fixed to the second lens frame 17. Thereby, the optical axis of the first lens frame 16 is aligned with the optical axis of the second lens frame 17, and the adjustment of the optical axis is completed. Thereafter, the objective optical system unit 11 is watertightly attached to the cover member by the adhesive, and entrance of foreign matter (i.e. moisture, water drops, dust) is prevented.

If the adjustment of the optical axis between the units is completed, light is emitted from the light source device, as described above. The light is made incident on the connector section, and is to the part to be observed from the illumination window 5 via the light guide fiber 12 which is passed through the universal cord 51, flexible tube portion 48 and bending section 2. Reflected light from the illuminated part to be observed is made incident on the observation window 4, and is reflected by the prism 20. The reflected light transmits through the first lens 21a, second lens 21b, third lens 21c, fourth lens 21d, optical filter 30 and cover lens 32. Further, infrared light of the reflected light is shaded by the optical filter 30, and only visible light of the reflective light is transmitted through the optical filter 30. The reflective light (visible light) transmitting through the optical filter 30 is transmitted through the cover glass 32, is focused on the light-receiving surface 42, and is converted to an electric signal by the image pickup element 31. The electric signal is amplified by the electric board 34, and is output to the monitor (not shown) via the signal cable 35. Thus, the electric signal is displayed as a subject image on the monitor. An image of the mucous membrane, which is clear and in focus without blurring, is displayed in enlarged scale on the monitor. Thereby, the endoscope 100 performs enlargement observation of the mucous membrane in a stable in-focus state.

As has been described above, in the present embodiment, the engaging portion 82 is engaged with the fixing slit 78, the position of disposition of the first lens frame 16 is adjusted, and the first lens frame 16 is aligned with and fixed to the second lens frame 17. Thereby, in this embodiment, the optical axis of the first lens frame 16, which is the front group optical frame of the objective optical system unit 11, can be precisely aligned, with simple structure, with the optical axis of the second lens frame 17 which is the rear group optical frame. Therefore, according to the present embodiment, an image that is captured by the image pickup element 31 is neither inclined nor twisted, and a good observation image can be obtained.

In the present embodiment, the optical axis adjustment between the first lens frame 16 and the second lens frame 17 can be performed with simple structure in multiple directions, without occupying a space. Therefore, in this embodiment, a good observation image without distortion can easily be obtained.

In the present embodiment, since the objective optical system unit 11 is constituted as a single unit, the performance of assembly to the distal end section body 1 is good and repair is easy.

In the present embodiment, the second lens frame 17 that is the rear group optical frame includes the optical axis restriction surface 86, fixing slit 78, lens frame hold portions 79a and 79b and screw hole 80, and the first lens frame 16 that is the front group optical frame includes the engaging portion 82 and projection portions 83. However, the structure is not limited to this example. For example, the first lens frame 16 may include the optical axis restriction surface 86, fixing slit 78, lens frame hold portions 79a and 79b and screw hole 80, and the second lens frame 17 may include the engaging portion 82 and projection portions 83. In other words, one of the first lens frame 16 and the second lens frame 17 includes the optical axis restriction surface 86, fixing slit 78 (gap portion), lens frame hold portions 79a and 79b and screw hole 80, and the other of the first lens frame 16 and the second lens frame 17 includes the engaging portion 82 and projection portions 83.

The aligning/fixing of the first lens frame 16 to the second lens frame 17 is not necessarily limited to the above.

For example, in a first modification, lens frame hold portions 79a and 79b, as shown in FIG. 6A, may be used. The lens frame hold portion 79a, 79b is a fixing portion which is different from the screw 77 and is substituted for the screw 77, and has an urging force in the Y axis direction. Two-dot-and-dash lines in FIG. 6A indicate the positions of end portions of the lens frame hold portions 79a and 79b at a time before the engaging portion 82 is engaged with the fixing slit 78. Specifically, in this modification, the length of the fixing slit 78 (the distal-end-side width of the fixing slit 78) in the Y axis direction is less than the length of the engaging portion 82 (the width of the engaging portion 82). Alternatively, even if the length is, conversely, greater at a time of unit components, the length may be decreased by slight collapsing at a time of assembly.

Thus, the lens frame hold portions 79a and 79b are urged in a direction away from each other in the Y axis direction, and the fixing slit 78 is slightly widened in the Y axis direction. In this state, the engaging portion 82 is inserted in the fixing slit 78. Thereby, the lens frame hold portions 79a and 79b hold the projection portions 83, and hold the engaging portion 82 by the urging force. In this manner, the second lens frame 17 holds the first lens frame 16.

In this hold state, the optical adjustment is performed, as has been described with reference to FIG. 4A and FIG. 4B, and the first lens frame 16 and the second lens frame 17 are watertightly bonded by the adhesive over the entire circumference and are completely fixed. Thereby, as shown in FIG. 6B, the first lens frame 16 is aligned with and fixed to the second lens frame 17.

If the complete fixation is performed, partial bonding may be adopted without a problem in terms of the optical performance. Besides, if the urging force of the lens frame hold portions 79a and 79b is strong, the fixation may be performed by only the urging force of the lens frame hold portions 79a and 79b, without coating the adhesive.

As described above, in the present modification, since the urging force of the lens frame hold portions 79a and 79b is used, the first lens frame 16 can easily be aligned and fixed. Therefore, in the present modification, the optical axis of the first lens frame 16 and the optical axis of the second lens frame 17 can precisely be aligned, and a good observation image can be obtained.

In addition, in this modification, since the screw 77 is not used, the manufacturing cost can be reduced. In addition, it is possible to prevent displacement between the aligned optical axes of the first lens frame 16 and second lens frame 17 due to the screw 77, which would occur if the screw 77 is used for alignment and fixing.

In a second modification, as shown in FIG. 7A, for example, two screws 77 may be used. Screw holes 80a and 80b, which communicate with the fixing slit 78, are formed in, and penetrate, the lens frame hold portions 79a and 79b. The screw holes 80a and 80b are opposed to each other.

In the present modification, the length of the fixing slit 78 (the width of the fixing slit 78) in the Y axis direction is greater than the length of the engaging portion 82 (the width of the engaging portion 82). In other words, the first lens frame 16 is movable in the Y axis direction from the state shown in FIG. 4A or FIG. 43.

When the engaging portion 82 is engaged in the fixing slit 78, the two screws 77 are engaged in the screw holes 80 in the Y axis direction and touch on the first lens frame 16. Thereby, the screws 77 align the first lens frame 16 with the second lens frame 17 and integrally fix the first lens frame 16 to the second lens frame 17. Thus, the two screws 77 slightly adjust the position of disposition of the first lens frame 16 in the Y axis direction, relative to the second lens frame 17.

Hence, in the present modification, the position of disposition of the first lens frame 16 can be adjusted in a greater number of directions. In addition, in the present modification, when the first lens frame 16 is aligned by the two screws 77, the first lens frame 16 can be fixed more firmly. Therefore, in the present modification, the optical axis of the first lens frame 16 and the optical axis of the second lens frame 17 can precisely be aligned, and a good observation image can be obtained.

Next, a second embodiment of the present invention is described with reference to FIG. 8 to FIG. 12. The same structural parts as in the first embodiment are denoted by the same reference numerals as in the first embodiment, and a description is omitted.

In a side-viewing electronic endoscope according to the present embodiment, an objective optical system unit 11 includes a zoom mechanism which can vary a focal length. Thus, the structures of the objective optical system unit 11 and the operation section 50 in the present embodiment are different from those in the first embodiment. The other structural parts are substantially similar, so a detailed description is omitted.

Figure 10:
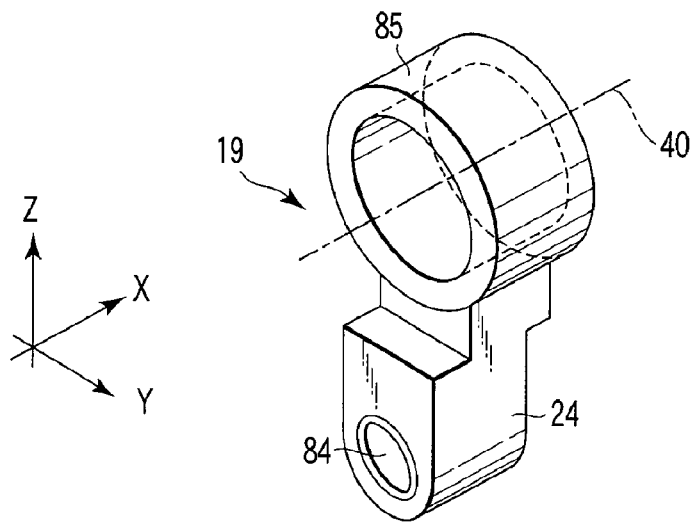
FIG. 10 is a perspective view of a fourth lens frame.

The objective optical system unit 11 of the present embodiment is a single unit, like the first embodiment. The objective optical system unit 11 is composed of four small units, namely, a first lens frame 16, a second lens frame 17, a third lens frame 18, and a fourth lens frame 19 which is shown in FIG. 10 and will be described later.

Like the first embodiment, in the first lens frame 16, there are disposed an observation window 4, a prism 20 and a first lens 21a. A stopper surface 39, which restricts a wide-angle-side movement range (to be described later) of the fourth lens frame 19, is integrally formed on the first lens frame 16.

The fourth lens frame 19 can be advanced/retreated, relative to the second lens frame 17, by a proximal-side operation by, for example, a zoom operation section 49.

Figure 8:
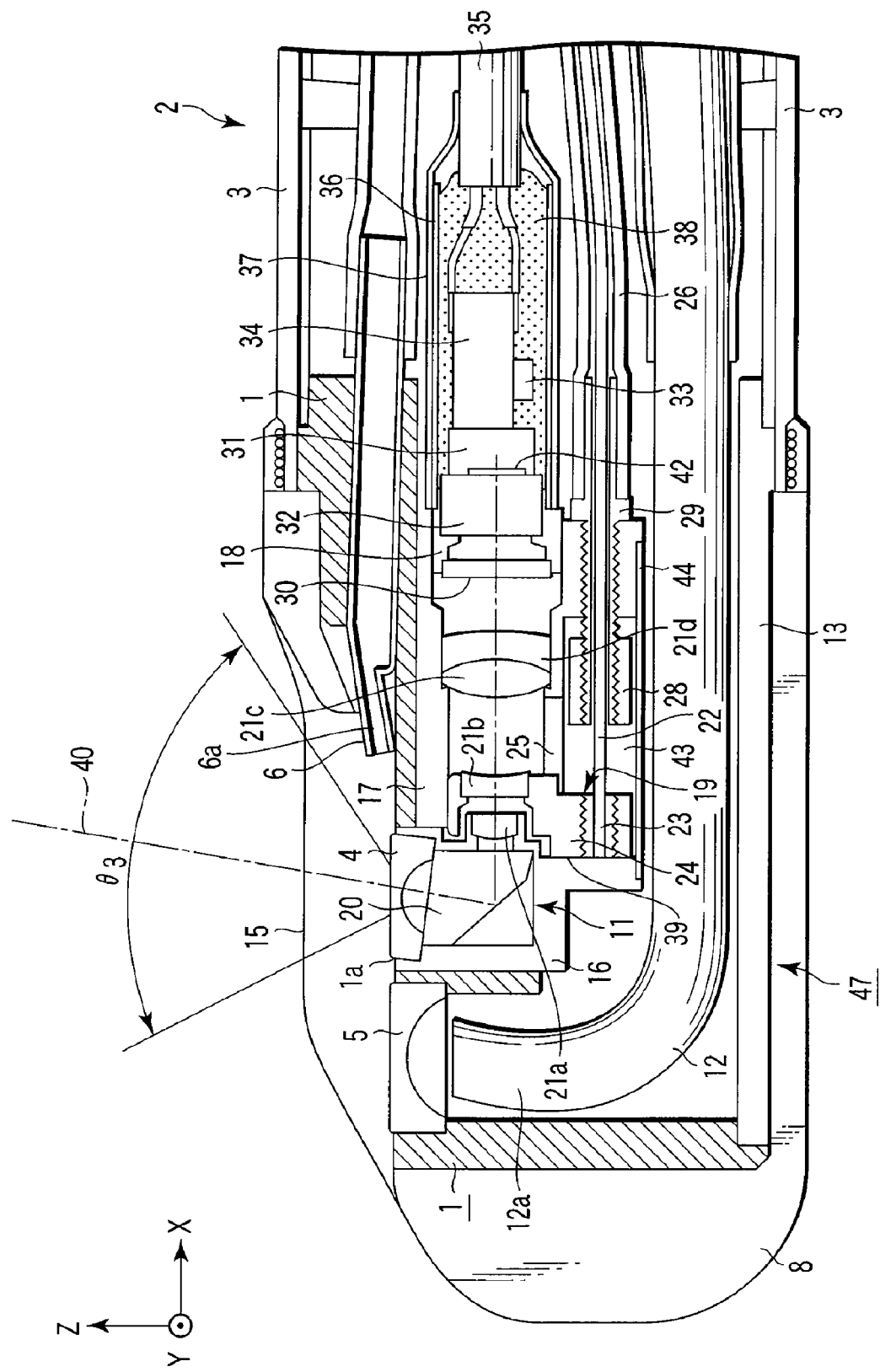
FIG. 8 is a cross-sectional view of a distal end section of a side-viewing electronic endoscope according to a second embodiment of the present invention.
Figure 9:
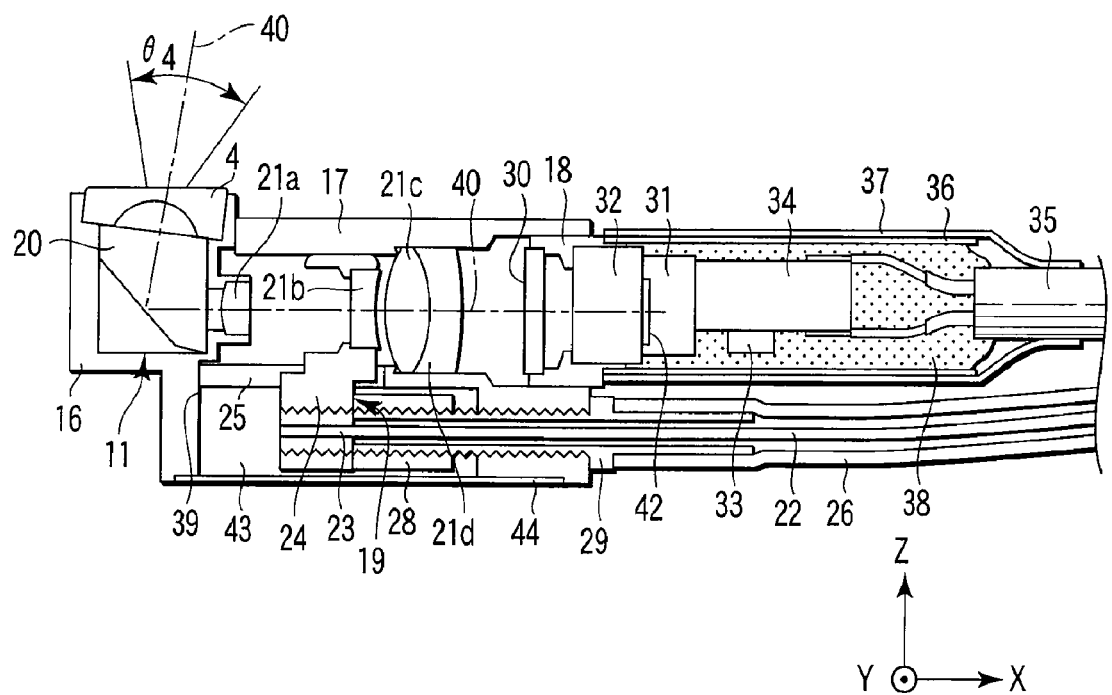
FIG. 9 is a cross-sectional view of an objective optical system unit shown in FIG. 8.

Specifically, the fourth lens frame 19 is provided with an arm portion 24 which is movable between the stopper surface 39 and a stopper 28 (to be described later) in the optical axis direction by means of a zoom operation wire 22, as shown in FIG. 8 and FIG. 9. As shown in FIG. 10, the arm portion 24 includes a lens barrel portion 85 which is a substantially circular cylindrical lens hold portion for holding the second lens 21b, and a wire attachment portion 84 to which a distal end 23 of the zoom operation wire 22 is fixed.

The zoom operation wire 22 is pushed and pulled, and the arm portion 24 is moved between the stopper surface 39 and stopper 28 (to be described later) in the X axis direction. Thereby, the second lens 21b advances/retreats in the optical axis direction, and the focal length of the objective optical system unit 11 varies. As described above, in the present embodiment, the objective optical system unit 11 includes the zoom mechanism.

Preferably, the length of the arm portion 24 in the Z axis direction should be so small that the lens barrel portion 85 can smoothly move. The arm portion 24 extends toward the position of disposition of the light guide fiber 12. In addition, as shown in FIG. 8, the arm portion 24 touches on the stopper surface 39, and thereby the wide-angle-side movement range is restricted. Specifically, the angle of view field, θ3, in the maximum wide-angle state shown in FIG. 8 is set by the touch of the arm portion 24 upon the stopper surface 39.

In the second lens frame 17, a slit 25, along which the arm portion 24 slides, is formed in the direction of the axis of the second lens frame 17 (i.e. the axis of the objective optical system unit 11) over a range between a distal end and an intermediate part of the second lens frame 17.

In addition, in the second lens frame 17, like the first embodiment, there are disposed a second lens 21b, a third lens 21c and a fourth lens 21d.

In the second lens frame 17, a mouthpiece 29 is fixed to a proximal end of the second lens frame 17 in a manner to penetrate in the optical axis direction. A guide member 26, which guides the zoom operation wire 22 to the arm portion 24, is attached to the mouthpiece 29. A stopper 28, which restricts the enlargement-side movement range of the fourth lens frame 19, is adjustably fixed on the distal end side of the mouthpiece 29. Specifically, the arm portion 24 touches on the stopper 28, and thereby the angle of view field, θ4, in the maximum enlargement state shown in FIG. 9 is set.

The third lens frame 18 is substantially similar to that in the above-described first embodiment.

Like the first embodiment, the first lens frame 16 is optically aligned with, and bonded and fixed to, the distal end side of the second lens frame 17.

In addition, like the first embodiment, the third lens frame 18 is optically aligned with, and bonded and fixed to, the second lens frame 17.

The arm portion 24 advances/retreats along the inner surface of the second lens frame 17 in the optical axis direction, as described above, by a remote control by means of the zoom operation wire 22. When wide-angle observation is performed as shown in FIG. 8, the arm portion 24, as described above, slides along the slit 25 and moves toward the stopper surface 39. In the case where enlargement observation is performed, as illustrated in FIG. 9, the arm portion 24 slides along the slit 25 and moves toward the stopper 28. In short, the fourth lens frame 19 (arm portion 24) slides along the slit 25 and advances/retreats between the stopper surface 39 and the stopper 28.

As has been described above, the zoom operation wire 22, slit 25, stopper 28 and stopper surface 39 constitute a movement mechanism which moves the arm portion 24 in the optical axis direction, thereby moving the second lens 21*b* in the optical axis direction.

Like the first embodiment, a dot-and-dash line in FIG. 8 indicates the optical axis 40. The optical axis 40 is reflected by the prism 20 and made substantially parallel with the axial direction of the objective optical system unit 11 within the objective optical system unit 11, and is focused on the light-receiving surface 42.

A subject image focused on the light-receiving surface 42 is converted, as in the first embodiment, to an electric signal by the image pickup element 31, and then amplified and transmitted to the video processor (not shown) via the signal cable 35. Further, the subject image is subjected to signal processing in the video processor and is displayed as an observation image on the monitor (not shown).

In the objective optical system unit 11 in the present embodiment, the coupling parts between the first lens frame 16, second lens frame 17, third lens frame 18 and fourth lens frame 19, a space 43 in which the arm portion 24 is advanced/retreated by the zoom operation wire 22, and peripheral parts of these four units are shielded by a cover member 44. An adhesive (not shown) is coated on end portions of the cover member 44 over the entire region. The cover member 44 is bonded to the objective optical system unit 11 by the adhesive. Thereby, the cover member 44 prevents foreign matter (i.e. moisture, water drops, dust) from entering the objective optical system unit 11 including the coupling parts from the outside of the objective optical system unit 11.

The angle (angle of view field) θ3 in FIG. 8 indicates the angle of view field in the maximum wide-angle state. At this time, the arm portion 24 touches on the stopper surface 39. The whole lens structure is not limited to that shown in FIG. 8. In the present embodiment, like the first embodiment, the endo-therapy product raising base (not shown) is stored in the endo-therapy product projection port (not shown).

The angle (angle of view field) θ4 in FIG. 9 indicates the angle of view field in the maximum enlargement state, as described above. At this time, the arm portion 24 moves (retreats) to the proximal end side in the X axis direction and touches on the stopper 28. The direction of the optical axis 40 at this time is the same as in the state shown in FIG. 8, but the angle (angle of view field) θ4 in FIG. 9 is less than the angle of view field, θ3, in FIG. 8 (θ3 >θ4).

For example, in the maximum wide-angle state shown in FIG. 8, the enlargement magnification on the monitor of, e.g. 14 inches is about 30. In the maximum enlargement state shown in FIG. 9, the enlargement magnification on the monitor of, e.g. 14 inches is about 80.

Figure 11:
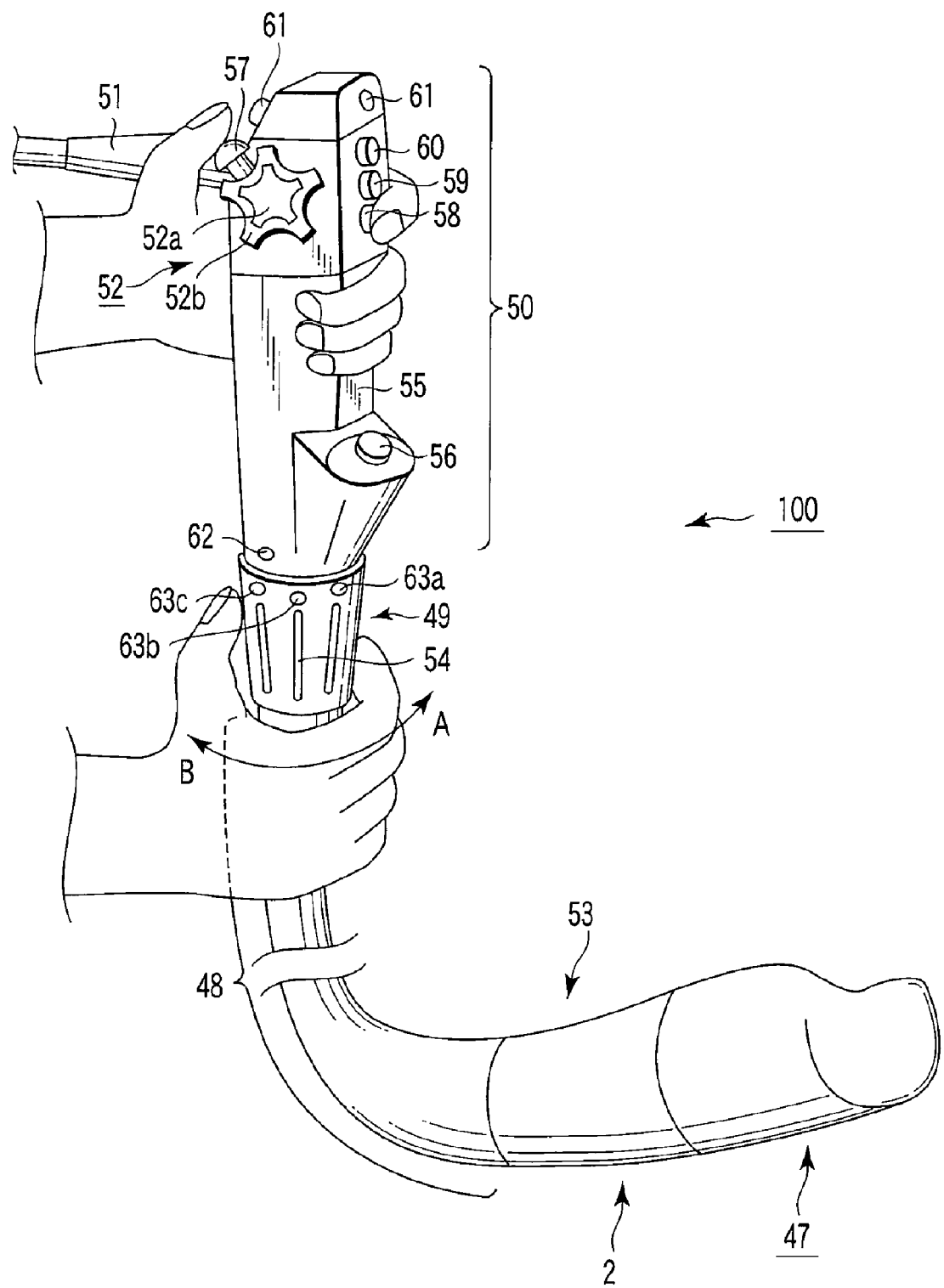
FIG. 11 is a schematic perspective view of the endoscope according to the second embodiment.

As is shown in FIG. 11, a zoom operation section 49, which performs a zoom operation, is disposed between the operation section 50 and the proximal-side end of the insertion section 53. The zoom operation section 49 is coupled to the proximal end of the insertion section 53 and to the operation section 50.

The zoom operation section 49 is provided with a zoom ring 54 which is movable rotationally in a circumferential direction about the insertion direction of the insertion section 53. If the zoom ring 54 is moved rotationally in a direction A (counterclockwise as viewed from the hold portion 55 side), the zoom operation wire 22 is pulled from the state shown in FIG. 8 and the fourth lens frame 19 moves (retreats) toward the stopper 28. If the fourth lens frame 19 touches on the stopper 28, as shown in FIG. 9, maximum enlargement observation is enabled.

If the zoom ring 54 is moved rotationally in a direction B (clockwise as viewed from the hold portion 55 side), the zoom operation wire 22 is pushed from the state shown in FIG. 9 and the fourth lens frame 19 moves (advances) toward the stopper surface 39. If the fourth lens frame 19 touches on the stopper surface 39, as shown in FIG. 8, maximum wide-angle observation is enabled.

The zoom ring 54 is provided with indices 63*a*, 63*b* and 63*c* which indicate enlargement magnification ratios by numerals, etc. The operation section 50 is provided with an index 62 in the vicinity of the zoom operation section 49, for alignment with the indices 63*a*, 63*b* and 63*c*. Specifically, if the zoom ring 54 is moved rotationally and any one of the indices 63*a*, 63*b* and 63*c* is aligned with the index 62, the monitor (not shown) of, e.g. 14 inches displays an observation image with a magnification corresponding to the index 63.

A cam mechanism (not shown) is built in the zoom operation section 49. The cam mechanism converts moving rotational movement of the zoom ring 54 to a linear advancing/retreating movement of the zoom operation wire 22. In the present embodiment, the structures are not necessarily limited to the above.

Since the objective optical system unit 11 includes the zoom mechanism, the external appearance of the objective optical system unit 11 in the present embodiment, as shown in FIG. 12A and FIG. 12B, is different from the external appearance of the objective optical system unit 11 in the first embodiment, as shown in FIG. 3A and FIG. 3B. However, the coupling structure between the first lens frame 16 and second lens frame 17 is substantially the same as that in the first embodiment.

Accordingly, the method of aligning the position of disposition of the first lens frame 16 relative to the second lens frame 17 and adjusting the optical axis in the present embodiment is substantially the same as the method in the first embodiment, so a detailed description of the method is omitted here.

In the case where the zoom mechanism is used, if the zoom ring 54 is moved rotationally in the direction B and the index 63*a* is aligned with the index 62, the zoom operation wire 22 is pushed and the fourth lens frame 19 advances and touches on the stopper surface 39, as shown in FIG. 8. Thus, the distal end section 47 is set in the maximum wide-angle state. In this state, the endoscope 100 captures an image of, for example, the mucous membrane (subject), which is the part to be observed in the body cavity, by means of the image pickup element 31 via the observation window 4. The captured image is displayed on the monitor, and the mucous membrane is probed.

Subsequently, the bending section 2 is bent by the bending operation knob 52 and the operation wire (not shown), and the insertion section 53 is pushed and pulled. Thus, the distal end section 47 is moved close to the mucous membrane.

Thereafter, if the zoom ring 54 is moved rotationally in the direction A and the index 63*c* is aligned with the index 62 as shown in FIG. 11, the zoom operation wire 22 is pulled and the fourth lens frame 19 retreats and touches on the stopper 28, as shown in FIG. 9. Thus, the distal end section 47 is set in the maximum enlargement state. In this state, the endoscope 100 captures an image of, for example, the mucous membrane (subject), which is the part to be observed in the body cavity, by means of the image pickup element 31 via the observation window 4. Thereby, an image of the mucous membrane, which is clear and in focus without blurring, is displayed in enlarged scale on the monitor. Thus, the endoscope 100 performs enlargement observation of the mucous membrane in a stable in-focus state.

According to the present embodiment, as described above, even with the side-viewing endoscope having the zoom mechanism in which the second lens 21*b* moves in the optical axis direction, the same advantageous effects as in the above-described first embodiment can be obtained.

Next, a third embodiment of the present invention is described with reference to FIG. 13A, FIG. 13B and FIG. 14. The same structural parts as in the first and second embodiments are denoted by the same reference numerals as in the first and second embodiments, and a description is omitted.

The above-described first and second embodiments relate to the side-viewing electronic endoscopes, whereas the present embodiment relates to a forward-viewing electronic endoscope. Accordingly, the structure of the objective optical system unit 11 of the present embodiment differs from the structure of the objective optical system unit 11 of the first embodiment. The other structural parts are substantially similar, so a detailed description is omitted.

A prism 20 is not built in the objective optical system unit 11. The observation window 4 is disposed behind the first lens 21*a* in the direction of travel of reflective light. The optical filter 30 is disposed between the observation window 4 and the first lens 21*a*. The other structural parts are substantially similar to those shown in FIG. 1, FIG. 3A, FIG. 3B and FIG. 5.

Figure 13B:
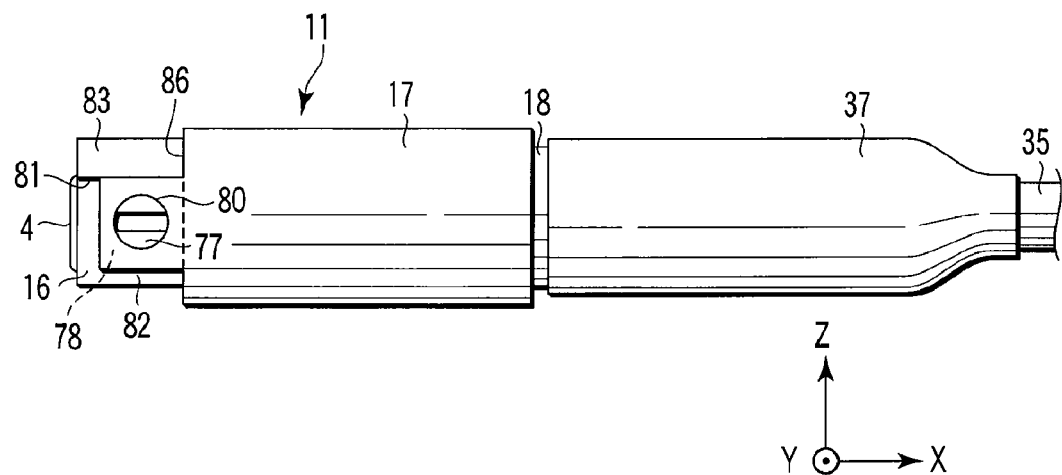
FIG. 13B is a side view of the objective optical system unit.

As shown in FIG. 13A and FIG. 13B, since the objective optical system unit 11 in the present embodiment is of the forward-viewing type, this objective optical system unit 11 is different from the objective optical system unit 11 in the first embodiment, which is of the side-viewing type, as shown in FIG. 3A and FIG. 3B. However, the coupling structure between the first lens frame 16 and the second lens frame 17 is substantially the same as in the first embodiment.

Accordingly, the method of aligning the position of disposition of the first lens frame 16 relative to the second lens frame 17 and adjusting the optical axis in the present embodiment is substantially the same as the method in the first embodiment, so a detailed description of the method is omitted here.

According to the present embodiment, as described above, even with the forward-viewing endoscope, the same advantageous effects as in the above-described first embodiment can be obtained.

Figure 14:
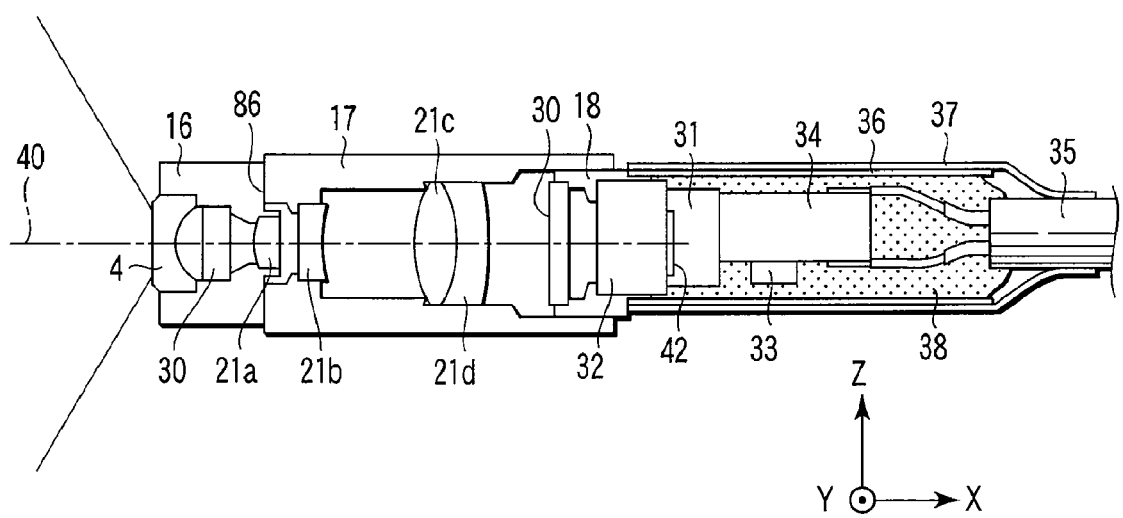
FIG. 14 is a cross-sectional view of the objective optical system unit shown in FIG. 13B.

The objective optical system unit 11 shown in FIG. 14 according to the present embodiment may include a zoom mechanism which is substantially similar to the zoom mechanism in the second embodiment. The whole lens structure is not limited to that shown in FIG. 14. In the present embodiment, like the first embodiment, the endo-therapy product raising base (not shown) is stored in the endo-therapy product projection port (not shown).

The second and third embodiments may be configured by combining the above-described modifications of the first embodiment.

The present invention is not limited directly to the above-described embodiments. In practice, the structural elements can be modified and embodied without departing from the spirit of the invention. Various inventions can be made by properly combining the structural elements disclosed in the embodiments.

Additional Description (Item 1) An endoscope comprising:
a front group optical frame which holds a first objective optical system;
a rear group optical frame which holds a second objective optical system and is disposed in front of the front group optical frame in a direction of travel of light;
an objective optical system which is composed of at least two optical frames which are the front group optical frame and the rear group optical frame;
an optical axis in the second objective optical system;
a Y axis which is perpendicular to an axial direction of the optical axis;
a Z axis which is perpendicular to the axial direction of the optical axis and an axial direction of the Y axis;
a front group engaging section which is formed on the front group optical frame;
a rear group engaging section which is formed on the rear group optical frame and is engaged with the front group engaging section, there by to couple the front group optical frame and the rear group engaging section;
adjusting means for restricting, when the front group engaging section and the rear group engaging section are engaged and the front group optical frame and the rear group engaging section are coupled, rotation of the front group optical frame in a circumferential direction about the axial direction of the optical axis, relative to the rear group optical frame, moving the front group optical frame in the axial direction of the optical axis, relative to the rear group optical frame, and moving rotationally the front group optical frame in a circumferential direction about the axial direction of the Y axis, relative to the rear group optical frame, thereby adjusting a position of disposition of the front group optical frame relative to the rear group optical frame; and
a fixing section which integrally fixes the front group optical frame, the position of disposition of which is adjusted by the adjusting means, to the rear group optical frame.

(Item 2) The endoscope according to item 1, wherein the adjusting means moves the front group optical frame in an axial direction of the Z axis, relative to the rear group optical frame, thereby adjusting the position of disposition of the front group optical frame relative to the rear group optical frame.

(Item 3) The endoscope according to item 2, wherein the adjusting means includes, in the rear group optical frame, a first restriction section which restricts the position of disposition of the front group optical frame which moves in the axial direction of the optical axis, a second restriction section which restricts the position of disposition of the front group optical frame which moves in the axial direction of the Y axis, and a third restriction section which restricts the position of disposition of the front group optical frame which moves in the axial direction of the Z axis.

(Item 4) The endoscope according to item 3, wherein one of the front group engaging section and the rear group engaging section includes a pair of hold portions which are disposed along the axial direction of the optical axis and are opposed to each other, and a gap portion which is interposed between the hold portions in the axial direction of the Y axis, thereby to hold the other of the front group engaging section and the rear group engaging section, and
the other of the front group engaging section and the rear group engaging section includes an engaging portion which is engaged with the gap portion and projection portions which are held by the hold portions when the engaging portion is engaged with the gap portion.

(Item 5) The endoscope according to item 4, wherein the endoscope is of a side-viewing type including a prism in the first objective optical system.

(Item 6) The endoscope according to item 2, wherein the fixing section includes a screw.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   a front group optical frame which holds a first objective optical system;
   a rear group optical frame which holds a second objective optical system;
   an objective optical system which is composed of at least two optical frames which are the front group optical frame and the rear group optical frame;
   a front group engaging section which is formed on the front group optical frame;
   a rear group engaging section which is formed on the rear group optical frame and is to be engaged with the front group engaging section;
   coupling support means for engaging the front group engaging section and the rear group engaging section, thereby coupling and supporting the front group optical frame relative to the rear group optical frame such that rotation of the front group optical frame about an optical axis, relative to the rear group optical frame, is restricted, the front group optical frame is adjustably movable along an optical axis direction relative to the rear group optical frame, and the front group optical frame is adjustably movable rotationally about an axis perpendicular to the optical axis, relative to the rear group optical frame; and
   a fixing section which integrally fixes the front group optical frame and the rear group optical frame, positions of disposition of which are adjusted by the coupling support means, wherein
   the rear group engaging section includes portions configured to exert an urging force on a portion of the front group engaging section to fix the front and rear group optical frames together in a direction perpendicular to the optical axis of the rear group optical frame,
   a slit in the rear group engaging section with a length of the slit being shorter than a length of a portion of the front group engaging section held in the slit of the rear engaging section, and
   the rear group engaging section is configured to serve as the fixing section.

2. The endoscope according to claim 1, wherein the coupling support means couples and supports the front group optical frame relative to the rear group optical frame such that the front group optical frame is also adjustably movable in a direction perpendicular to the optical axis, relative to the rear group optical frame.

3. The endoscope according to claim 2, wherein the coupling support means includes an optical axis direction restriction section which restricts a position of the front group optical frame in the optical axis direction to a predetermined position, relative to the rear group optical frame, and a perpendicular direction restriction section which restricts the position of the front group optical frame in a direction perpendicular to the optical axis to a predetermined position, relative to the rear group optical frame.

4. The endoscope according to claim 3, wherein one of the front group engaging section and the rear group engaging section includes a slit which is formed along the optical axis direction, and the other of the front group engaging section and the rear group engaging section includes an engaging portion which is engaged with the slit and projection portions which come in contact with the slit.

5. The endoscope according to claim 4, wherein the endoscope is a side-viewing endoscope which includes a prism as the first objective optical system and includes no prism as the second objective optical system.

6. An endoscope comprising:
   a front group optical frame which holds a first objective optical system;
   a rear group optical frame which holds a second objective optical system and is disposed in front of the front group optical frame in a direction of travel of light;
   an objective optical system which is composed of at least two optical frames which are the front group optical frame and the rear group optical frame;
   an optical axis in the second objective optical system;
   a Y axis which is perpendicular to an axial direction of the optical axis;
   a Z axis which is perpendicular to the axial direction of the optical axis and an axial direction of the Y axis;
   a front group engaging section which is formed on the front group optical frame;
   a rear group engaging section which is formed on the rear group optical frame and is engaged with the front group engaging section, thereby to couple the front group optical frame and the rear group engaging section;
   adjusting means for restricting, when the front group engaging section and the rear group engaging section are engaged and the front group optical frame and the rear group engaging section are coupled, rotation of the front group optical frame in a circumferential direction about the axial direction of the optical axis, relative to the rear group optical frame, moving the front group optical frame in the axial direction of the optical axis, relative to the rear group optical frame, and moving rotationally the front group optical frame in a circumferential direction about the axial direction of the Y axis, relative to the rear group optical frame, thereby adjusting a position of disposition of the front group optical frame relative to the rear group optical frame; and
   a fixing section which integrally fixes the front group optical frame, the position of disposition of which is adjusted by the adjusting means, to the rear group optical frame, wherein
   the rear group engaging section includes portions configured to exert an urging force on a portion of the front group engaging section to fix the front and rear group optical frames together in a direction of the Y axis,
   a slit in the rear group engaging section with a length of the slit of the rear group engaging section being shorter than a length of a portion of the front group engaging section held in the slit of the rear engaging section, and
   the rear group engaging section is configured to serve as the fixing section.

7. The endoscope according to claim 6, wherein the adjusting means moves the front group optical frame in an axial direction of the Z axis, relative to the rear group optical frame, thereby adjusting the position of disposition of the front group optical frame relative to the rear group optical frame.

8. The endoscope according to claim 7, wherein the adjusting means includes, in the rear group optical frame, a first restriction section which restricts the position of disposition of the front group optical frame which moves in the axial direction of the optical axis, a second restriction section which restricts the position of disposition of the front group optical frame which moves in the axial direction of the Y axis, and a third restriction section which restricts the position of disposition of the front group optical frame which moves in the axial direction of the Z axis.

9. The endoscope according to claim 8, wherein one of the front group engaging section and the rear group engaging section includes a pair of hold portions which are disposed along the axial direction of the optical axis and are opposed to each other, and a gap portion which is interposed between the hold portions in the axial direction of the Y axis, thereby to hold the other of the front group engaging section and the rear group engaging section, and the other of the front group engaging section and the rear group engaging section includes an engaging portion which is engaged with the gap portion and projection portions which are held by the hold portions when the engaging portion is engaged with the gap portion.

10. The endoscope according to claim 9, wherein the endoscope is of a side-viewing type including a prism in the first objective optical system.

\* \* \* \* \*